United States Patent [19]

Katz et al.

[11] 4,453,546

[45] Jun. 12, 1984

[54] SCLERAL DEPRESSOR

[75] Inventors: Norman N. K. Katz, Beltsville; Vincent A. Przybyla, Jr., Huntingtown, both of Md.

[73] Assignee: The United States of America as reprsented by the Secretary of the Army, Washington, D.C.

[21] Appl. No.: 423,575

[22] Filed: Sep. 27, 1982

[51] Int. Cl.³ ............................................. A61B 17/00
[52] U.S. Cl. ............................................. 128/303 R
[58] Field of Search ...................... 128/303 R, 305, 20, 128/15, 304, 757, 759, 3, 16, 67, 355, 323; 46/6; 29/278; 30/316, 301

[56] References Cited

U.S. PATENT DOCUMENTS

| 7,872 | 4/1898 | Gabe | 128/15 |
|---|---|---|---|
| 668,823 | 2/1901 | Pilling | 128/15 |
| 1,187,079 | 6/1916 | Miller et al. | 128/15 |
| 2,034,299 | 3/1936 | Jacobs | 128/323 |
| 2,117,312 | 5/1938 | Gauly | 128/303 R |
| 2,224,575 | 12/1940 | Montalvo-Guenard | 128/303 R |
| 2,555,076 | 5/1951 | Crossley | 128/303 R |
| 2,618,886 | 11/1952 | Wagner | 46/6 |
| 2,885,537 | 5/1959 | Wood, Jr. | 128/16 |
| 3,132,887 | 5/1964 | Martinez | 128/303 R |
| 3,384,088 | 5/1968 | Miseo | 128/323 |
| 3,706,106 | 12/1972 | Leopoldi | 128/305 |
| 4,222,382 | 9/1980 | Antonsson et al. | 128/303 R |

OTHER PUBLICATIONS

*The Surgical Armamentarium*, (Instruments-Professional Equipment), American V. Mueller, (Div. of American Hospital Supply Corp.), 1980.

*Primary Examiner*—Richard J. Apley
*Assistant Examiner*—Harry J. Macey
*Attorney, Agent, or Firm*—John H. Raubitschek; Arthur I. Spechler; Werten F. W. Bellamy

[57] ABSTRACT

An ophthalmic instrument for controlling eye position comprising a substantially oblong shaped blade that has a textured surface and that is formed with a hole substantially in the middle of the blade. In operation, the blade is manipulated by the operator to depress against the sclera of a patient's eye for either rotating or immobilizing the globe of the eye during examination. The instrument further comprises a handle, with optional pocket clip, which is attached to the blade at an offset angle to facilitate manipulation of the blade from a position that leaves the field substantially clear for the simultaneous use of other instruments, such as an opthalmoscope.

6 Claims, 5 Drawing Figures

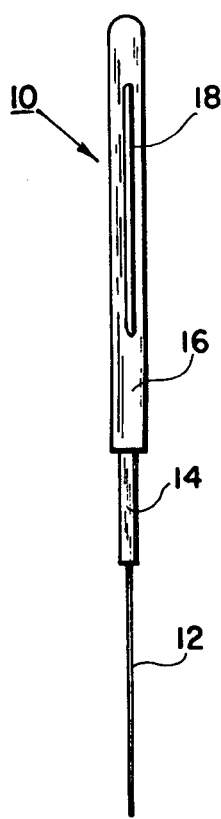
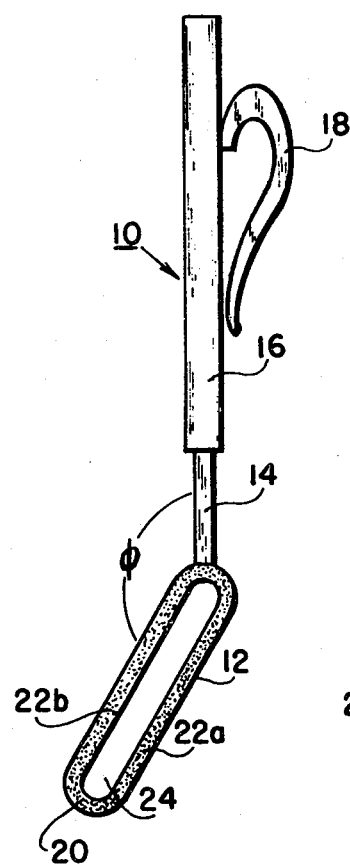
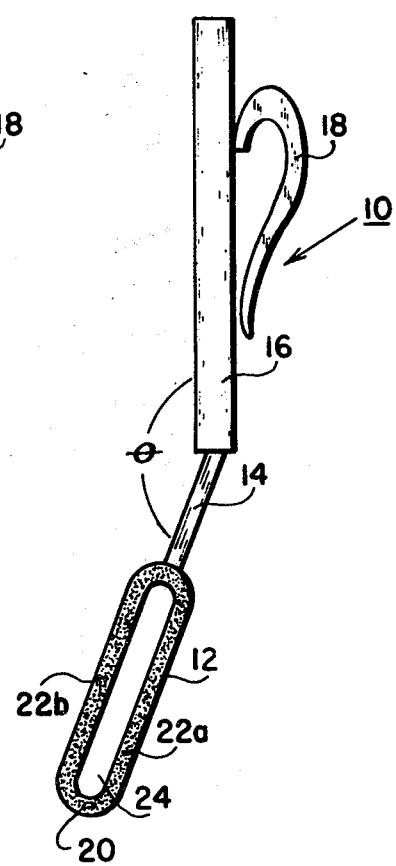
FIG. 1     FIG. 2     FIG. 3
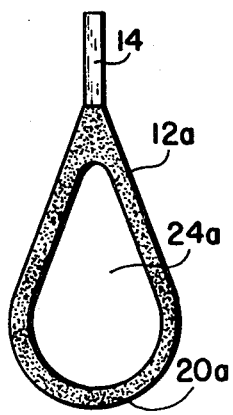
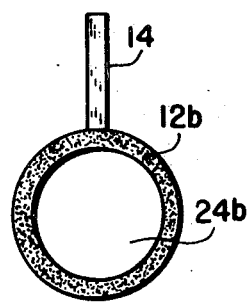
FIG. 4     FIG. 5

SCLERAL DEPRESSOR

The invention described herein may be manufactured, used and licensed by or for the Government for governmental purposes without the payment to use of any royalty thereon.

BACKGROUND OF THE INVENTION

The invention relates generally to hand-held ophthalmic instruments used to control eye position during an examination of the fundus of the eye. More particularly, the invention relates to scleral depressors which are pressed against the sclera during an eye examination to allow the examiner to rotate the globe of the eye into a desired position and hold it in such position. The present invention is particularly, through not exclusively, useful for fundus examination of infants having very small palpebral fissures.

DESCRIPTION OF THE PRIOR ART

During a fundus examination of the eye, and particularly during the study of areas of the retina such as the periphery, it is necessary for the examiner to have control over the position of the eye. One way which is frequently used to obtain the needed control is to press against the sclera of the eye with a depressor. Several scleral depressors have been designed for this purpose. For example, the Storz Instrument Company, on page 146 in their 12th edition of the Storz Eye Instruments catalog, illustrates several such depressors. In addition to these more conventional devices, some unconventional means, such as paper clips, safety pins, cotton tipped applicators and strabismus hooks are also used for the above stated purposes.

State-of-the-art scleral depressors, both conventional and unconventional, are used generally for the examination of adult patients but have several limitations when used on premature, new born and very small infants. They are not ideally suited for infant examination for the following general reasons: (a) the tips of these depressors are bulky and with a pediatric lid speculum in place it is often difficult to find adequate room to insert the instrument into the conjunctival sac; (b) undue pressure on the globe and compromise of the ocular circulation is therefore possible; and (c) these scleral depressors have smooth surfaces, slide on the globe, and will not rotate it to different examination positions. Additionally, both the conventional and unconventional scleral depressors are often difficult to use in conjunction with other instruments because they are not designed for operation from a position which will leave the field substantially clear for the simultaneous use of these instruments in the examination of the eye.

Some of the objects of this invention are to provide a safe and easily manipulated ophthalmic instrument which will give positive control over the position of the eye during fundus examination. Also, the invention overcomes many difficulties encountered during such examinations of infants where the bulk and configuration of oversized instruments hinder, and frequently preclude, their use.

A further object of this invention is to provide a scleral depressor which is compatible with the simultaneous use of other instruments, such as an indirect ophthalmoscope.

Still another object of the present invention is to provide a means for applying local pressure to the sclera to bring the temporal periphery of the fundus into view for examination.

SUMMARY OF THE INVENTION

A preferred embodiment of the invention includes an oblong shaped blade which is attached to a handle. The blade has a textured surface and is formed with an oblong shaped hole whose lengthwise axis is the same as that of the blade. Also, the blade is angled relative to the handle to allow manipulation of the blade from an offset position.

The novel features of this invention, as well as the invention itself, will be best understood from the accompanying drawings, taken together with the accompanying description, in which similar reference characters refer to similar parts, and in which:

BRIEF DESCRIPTION OF THE DRAWINGS

FIG. 1 is a side elevational view of the scleral depressor;

FIG. 2 is a front elevational view of the depressor;

FIG. 3 is a front elevational view of an alternate embodiment of the depressor;

FIG. 4 is a front elevational view of a portion of the scleral depressor showing an alternate embodiment of the blade; and FIG. 5 is a front elevational view of a portion of the scleral depressor showing a second alternate embodiment of the blade.

DESCRIPTION OF THE PREFERRED EMBODIMENT

Referring first to FIG. 1, the structural relationship between various elements of the depressor 10 are shown in profile. As seen in FIG. 1, a blade 12 is joined to a handle 16 by an interconnecting stem 14. An optional pocket clip 18, which can be attached to handle 16, is also shown in FIG. 1. As will be subsequently shown, incorporation of pocket clip 18 can facilitate operation of the depressor 10.

More detail on the interrelationship of the elements of the depressor 10 can be appreciated by now referring to FIG. 2. In FIG. 2, the blade 12 is shown to be in the shape of an elongated U. In this configuration, the tip 20 of blade 12 is the base of the U and the sides 22a and 22b of blade 12 are the sides of the U. In the preferred embodiment of the depressor 10, the tip 20 is substantially rounded and the sides 22a and b are straight and are substantially parallel. Also, as shown in FIG. 2, the sides 22a and b are integral with or rigidly joined, at their ends opposite tip 20, with stem 14 by any suitable means. In this manner the blade 12 is formed with an oblong shaped hole 24.

Referring now to FIG. 4 and FIG. 5, two alternate embodiments of the blade 12 are shown which will also serve the same objectives for the invention which have been stated above. In one alternate embodiment, as shown in FIG. 4, the blade 12a is formed in the shape of a teardrop. In this embodiment, the tip 20a of blade 12a is shaped substantially as described above for the blade 12 shown in FIG. 2. Here, however, the hole 24a, in order to conform with the shape of blade 12a, is also formed in the shape of a teardrop. Blade 12a may be integral with or attached to stem 14 by any suitable means. In still another embodiment, as shown in FIG. 5, the blade 12b can be formed into the shape of a circle. Hole 24b will also be in the shape of a circle and the blade 12b, as described in the other embodiments, is either integral with or attached to stem 14 by any suitable means.

The salient feature of any of the above described shapes for blade 12 is that there is a hole 24 which allows the sides of the blade 12 to grip the surface of the eye during operation of the depressor 10. Perhaps more importantly, each embodiment presents a blade 12 having rounded surfaces without edges. Thus, the blade 12 is devoid of sharp or pointed protrusions and the possibility of trauma to the eye during use of the depressor 10 is thereby reduced.

The blade 12, as described above for any of the embodiments should be made of a material having sufficient rigidity to prevent any substantial bending of the blade 12 during use of the depressor 10. Also, the sides 22a, b and the tip 20 of blade 12 should have a textured surface which will provide sufficient adhesion between the blade 12 and the globe of an eye so movement of the depressor 10 will control movement of the eye. Several methods, all well known in the art, can be used to roughen the surface of blade 12 for this purpose. For example, sand blasting has been demonstrated to be efficacious in providing a surface for blade 12 which will satisfy the operational requirements implied above. Care must be taken, however, to not make the blade 12 so rough in texture that its roughness will cause trauma to the eye during use of the depressor 10.

Referring again to FIG. 2, it can be seen that the axis of stem 14 is offset from the lengthwise axis of blade 12 by an obtuse angle $\phi$. In the construction of depressor 10, this angle $\phi$ can be varied. In fact the angle $\phi$ could be set at any value between ninety degrees (90°) and one hundred and eighty degrees (180°). The preferred embodiment, however, has angle $\phi$ of sufficient value to allow manipulation of the depressor 10 from a hand position which will leave a clear field near the eye being examined for the simultaneous use of other ophthalmic instruments. Experience would indicate that values of the angle $\phi$ in the range of one hundred and forty-five degrees (145°) to one hundred and seventy degrees (170°) are optimal. Nevertheless, as implied above, values outside this range may be equally efficacious for certain manipulations. It is also necessary to point out that the same objectives can be obtained by attaching the blade 12 to stem 14 so their lengthwise axes coincide. In this embodiment, the angle $\theta$ between the axis of handle 16 and the axis of stem 14, as shown in FIG. 3, can be varied according to the above description for the angle $\phi$ and for the same purposes. In either case, the angle $\theta$ or the angle $\phi$ should lie in the 145–170 degree range for the preferred embodiment of depressor 10. It is also evident that stem 14 can be bent until the angle between the axis of handle 16 and the length wise axis of blade 12 lies within the desired range.

As shown in the drawings the stem 14 is rigidly attached to one end of handle 16 by any suitable means. Also, as shown in the drawings, a pocket clip 18, may be attached to handle 16. The pocket clip 18, in addition to its obvious function of securing depressor 10 to the examiner's clothing when depressor 10 is not being used, can also serve to aid the examiner in stabilizing and controlling the manipulation of depressor 10. Pocket clip 18, in serving this purpose acts as a brace to inhibit rotation of the handle 16 in the examiner's hand.

Referring now to the embodiment of depressor 10 as shown in FIG. 2, the following dimensions can be used to more accurately describe the depressor 10. It must be recognized that the range of values given below are only representative, and not exclusive, of variations on the preferred embodiment which can be used for the purposes of the invention.

|  |  | Preferred Embodiment (example) | Range |
|---|---|---|---|
| Blade 12: | Length | 20 mm | 10 mm–30 mm |
|  | Width | 5 mm | 3 mm–7 mm |
| Hole 24: | Length | 18 mm | 9 mm–28 mm |
|  | Width | 4 mm | 2 mm–6 mm |
| Stem 14: | Length | 10 mm | 5 mm–20 mm |
| Handle 16: | Length | 100 mm | as desired |

It should be noted that when varying the dimensions of the blade 12 and hole 24, the thickness of the sides 22a and b and the thickness of the tip 20 should be substantially 0.5 mm. Again, this value is only representative. Values between 0.2 mm and 1 mm may be suitable depending upon the preference of the particular individual using depressor 10.

During the operation of the depressor 10 it is first suggested that a topical anesthesia be used on the eye. The tip 20 of blade 12 is inserted through the palpebral fissure and into the conjunctional sac. After insertion into the conjunctional sac, blade 12 is pressed against the sclera until a sufficient grip is established to enable control of the eye's position. The eye can then be moved without conjunctional trauma into the various examination positions.

For an examination of the peripheral fundus, tip 20 of depressor 10 can be pressed against the sclera to bring the peripheral fundus into the examiner's view. Use of depressor 10 for this manuever has proven to be more effective in consistently obtaining an adequate view of the peripheral fundus than the application of doll's head manuevers.

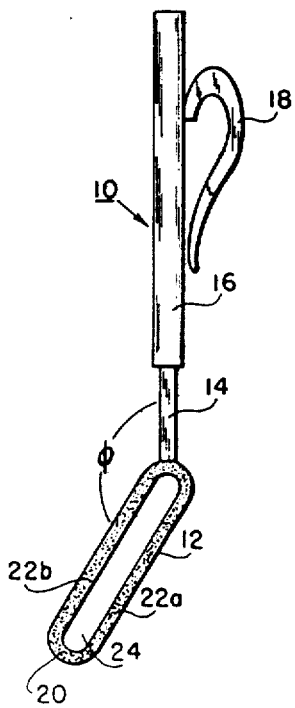

I claim:
1. A scleral depressor for controlling eye position comprising:
   a planar blade with a textured, non-smooth, uneven, pimply, roughened surface, formed with a hole and having a handle means adapted for pressing said surface against only the sclera of said eye to control eye position, and
   said handle means having an axis lying substantially in the plane of said blade, attached to said blade and angled therefrom at an angle between 145 degrees and 175 degrees.
2. A depressor as cited in claim 1 wherein said blade is oblong shaped.
3. A scleral depressor for controlling eye position comprising:
   a planar blade with a textured, non-smooth, uneven, pimply, roughened surface, formed with a hole and having a handle means adapted for pressing said surface against only the sclera of said eye for controlling eye position,
   said handle means rigidly attached to said blade and angled therefrom at an angle between 145 degrees and 170 degrees, and
   a pocket clip attached to said handle, said blade, said handle and said clip lying in substantially the same plane.
4. A depressor as cited in claim 3 wherein said blade is oblong shaped.
5. A depressor as cited in claim 3 wherein said blade is teardrop shaped.
6. A depressor as cited in claim 3 wherein said blade is circular shaped and adapted for pressing against only the sclera of said eye, the area of said hole being larger than the pupil of said eye.

* * * * *

UNITED STATES PATENT AND TRADEMARK OFFICE
CERTIFICATE OF CORRECTION

PATENT NO. : 4,453,546

DATED : June 12, 1984

INVENTOR(S) : Norman N. K. Katz et al.

It is certified that error appears in the above-identified patent and that said Letters Patent is hereby corrected as shown below:

The title page showing the illustrative figure should be deleted to appear as per attached title page.

Signed and Sealed this

Fifteenth Day of January 1985

[SEAL]

Attest:

GERALD J. MOSSINGHOFF

Attesting Officer

Commissioner of Patents and Trademarks

United States Patent [19]

Katz et al.

[11] 4,453,546
[45] Jun. 12, 1984

[54] SCLERAL DEPRESSOR

[75] Inventors: Norman N. K. Katz, Beltsville; Vincent A. Przybyla, Jr., Huntingtown, both of Md.

[73] Assignee: The United States of America as reprsented by the Secretary of the Army, Washington, D.C.

[21] Appl. No.: 423,575

[22] Filed: Sep. 27, 1982

[51] Int. Cl.³ .............................................. A61B 17/00
[52] U.S. Cl. ................................................ 128/303 R
[58] Field of Search ...................... 128/303 R, 305, 20, 128/15, 304, 757, 759, 3, 16, 67, 355, 323; 46/6; 29/278; 30/316, 301

[56] References Cited

U.S. PATENT DOCUMENTS

| 7,872 | 4/1898 | Gabe | 128/15 |
|---|---|---|---|
| 668,823 | 2/1901 | Pilling | 128/15 |
| 1,187,079 | 6/1916 | Miller et al. | 128/15 |
| 2,034,299 | 3/1936 | Jacobs | 128/323 |
| 2,117,312 | 5/1938 | Gauly | 128/303 R |
| 2,224,575 | 12/1940 | Montalvo-Guenard | 128/303 R |
| 2,555,076 | 5/1951 | Crossley | 128/303 R |
| 2,618,886 | 11/1952 | Wagner | 46/6 |
| 2,885,537 | 5/1959 | Wood, Jr. | 128/16 |
| 3,132,887 | 5/1964 | Martinez | 128/303 R |
| 3,384,088 | 5/1968 | Miseo | 128/323 |
| 3,706,106 | 12/1972 | Leopoldi | 128/305 |
| 4,222,382 | 9/1980 | Antonsson et al. | 128/303 R |

OTHER PUBLICATIONS

*The Surgical Armamentarium,* (Instruments–Professional Equipment), American V. Mueller, (Div. of American Hospital Supply Corp.), 1980.

*Primary Examiner*—Richard J. Apley
*Assistant Examiner*—Harry J. Macey
*Attorney, Agent, or Firm*—John H. Raubitschek; Arthur I. Spechler; Werten F. W. Bellamy

[57] ABSTRACT

An ophthalmic instrument for controlling eye position comprising a substantially oblong shaped blade that has a textured surface and that is formed with a hole substantially in the middle of the blade. In operation, the blade is manipulated by the operator to depress against the sclera of a patient's eye for either rotating or immobilizing the globe of the eye during examination. The instrument further comprises a handle, with optional pocket clip, which is attached to the blade at an offset angle to facilitate manipulation of the blade from a position that leaves the field substantially clear for the simultaneous use of other instruments, such as an opthalmoscope.

6 Claims, 5 Drawing Figures